United States Patent
Buehr

(10) Patent No.: US 9,423,410 B2
(45) Date of Patent: Aug. 23, 2016

(54) TRANSPORT DEVICE, SAMPLE DISTRIBUTION SYSTEM, AND LABORATORY AUTOMATION SYSTEM

(71) Applicant: Roche Diagnostics Operations, Inc., Indianapolis, IN (US)

(72) Inventor: Fritz Buehr, Kirchburg/Murr (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/619,332

(22) Filed: Feb. 11, 2015

(65) Prior Publication Data

US 2015/0233956 A1     Aug. 20, 2015

(30) Foreign Application Priority Data

Feb. 17, 2014   (DE) .................. 10 2014 202 838

(51) Int. Cl.
*G01N 21/00*    (2006.01)
*G01N 35/04*    (2006.01)

(52) U.S. Cl.
CPC ........ *G01N 35/04* (2013.01); *G01N 2035/0401* (2013.01); *G01N 2035/0477* (2013.01)

(58) Field of Classification Search
CPC ................... G01N 35/0098; G01N 35/1081; G01N 35/02
USPC .................................................. 422/65, 63
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,255,614 B1 | 7/2001 | Yamakawa et al. |
| 6,260,360 B1 | 7/2001 | Wheeler |
| 6,279,728 B1 | 8/2001 | Jung et al. |
| 6,429,016 B1 | 8/2002 | McNeil |
| 6,444,171 B1 | 9/2002 | Sakazume et al. |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Natalia Levkovich

(74) *Attorney, Agent, or Firm* — Roche Diagnostics Operations, Inc.

(57) ABSTRACT

A transport device for transporting a sample container along a transport surface is presented. The transport device comprises a permanent magnet, a holding unit and a receiving unit. This enables reliable transporting of sample containers by means of magnetic forces. A sample distribution system and a laboratory automation system are also presented.

4 Claims, 2 Drawing Sheets

(56) References Cited

U.S. PATENT DOCUMENTS

| | | |
|---|---|---|
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,850,914 B2 | 12/2010 | Veiner et al. |
| 7,858,033 B2 | 12/2010 | Itoh |
| 7,875,254 B2 | 1/2011 | Garton |
| 8,281,888 B2 | 10/2012 | Bergmann |
| 8,796,186 B2 | 8/2014 | Shirazi |
| 9,211,543 B2 | 12/2015 | Ohga et al. |
| 9,239,335 B2 | 1/2016 | Heise |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2005/0061622 A1 | 3/2005 | Martin |
| 2005/0109580 A1 | 5/2005 | Thompson |
| 2005/0194333 A1* | 9/2005 | Veiner .................. G01N 35/04 211/74 |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0271555 A1 | 12/2005 | Itoh |
| 2006/0000296 A1 | 1/2006 | Salter |
| 2006/0047303 A1 | 3/2006 | Ortiz et al. |
| 2007/0116611 A1 | 5/2007 | DeMarco |
| 2007/0210090 A1 | 9/2007 | Sixt et al. |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth |
| 2009/0142844 A1 | 6/2009 | Le Comte |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0312379 A1 | 12/2010 | Pedrazzini |
| 2011/0050213 A1 | 3/2011 | Furukawa |
| 2011/0172128 A1 | 7/2011 | Davies et al. |
| 2011/0186406 A1 | 8/2011 | Kraus |
| 2011/0287447 A1 | 11/2011 | Norderhaug |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1 | 8/2014 | Heise et al. |
| 2014/0234978 A1 | 8/2014 | Heise et al. |
| 2015/0233957 A1 | 8/2015 | Riether |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinkowski et al. |

FOREIGN PATENT DOCUMENTS

| | | |
|---|---|---|
| DE | 3909786 A1 | 9/1990 |
| DE | 102011090044 A1 | 7/2013 |
| EP | 0601213 A1 | 6/1994 |
| EP | 0775650 A1 | 5/1997 |
| EP | 0896936 A1 | 2/1999 |
| EP | 0916406 A2 | 5/1999 |
| EP | 2148117 A1 | 1/2010 |
| EP | 2327646 A1 | 6/2011 |
| EP | 2447701 A2 | 5/2012 |
| EP | 2502675 A1 | 9/2012 |
| GB | 2165515 A | 4/1966 |
| JP | S56-147209 A | 11/1981 |
| JP | 60-223481 A | 11/1985 |
| JP | 61-081323 A | 4/1986 |
| JP | S61-217434 A | 9/1986 |
| JP | S63-31918 A | 2/1988 |
| JP | S63-48169 A | 2/1988 |
| JP | 01-148966 A | 6/1989 |
| JP | 01-266860 A | 10/1989 |
| JP | H02-87903 A | 3/1990 |
| JP | 3-112393 A | 5/1991 |
| JP | 03-192013 A | 8/1991 |
| JP | H05-69350 A | 3/1993 |
| JP | H05-180847 A | 7/1993 |
| JP | 06-26808 A | 4/1994 |
| JP | 06-026808 A | 4/1994 |
| JP | 06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-145188 A | 7/2009 |
| JP | 2009-300402 A | 12/2009 |
| JP | 2013-172009 A | 9/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/064656 A1 | 5/2013 |
| WO | 2013/099647 A1 | 7/2013 |
| WO | 2013/169778 A1 | 11/2013 |
| WO | 2014/059134 A1 | 4/2014 |

\* cited by examiner

TRANSPORT DEVICE, SAMPLE DISTRIBUTION SYSTEM, AND LABORATORY AUTOMATION SYSTEM

CROSS-REFERENCE TO RELATED APPLICATIONS

This application claims priority to DE 10 2014 202 838.8, filed Feb. 17, 2014, which is hereby incorporated by reference.

BACKGROUND

The present disclosure generally relates to a transport device and, in particular, to a transport device for receiving and fixing a sample container and for transporting the sample container, to a sample distribution system, and to a laboratory automation system.

Sample containers are typically elongated vessels which are open at the one end, produced in the majority of cases from transparent glass or plastics material and are used for storing and for transporting in the majority of cases liquid samples. These types of samples are, for example, blood samples. In the case of laboratory automation systems, it is frequently necessary to transport samples in sample containers to a plurality of different stations of the laboratory automation system.

There is a need for to provide a transport device, a sample distribution system and a laboratory automation system that are simple to handle.

SUMMARY

According to the present disclosure, a transport device for receiving and fixing a sample container and for transporting the sample container between pre-analytical, analytical and/or post-analytical stations of a laboratory automation system is presented. The transport device can comprise at least one magnetically active element. The at least one magnetically active element can interact with a magnetic field such that a driving force is applied to the transport device. The magnetic field can be generated by at least one electromagnetic actuator. The transport device can further comprise a holding unit having a push-through region through which the sample container can be pushed in longitudinal direction. The holding unit can be formed such that the sample container, in the pushed-through state, can be fixed radially in the region of the holding unit. The transport device can also comprise a receiving unit spaced from the holding unit. The receiving unit can receive a bottom end of a pushed-through sample container. The receiving unit can be fixed to the bottom end of a pushed-through sample container in a radial manner.

In accordance with one embodiment of the present disclosure, a sample distribution system is presented that can utilize the transport device.

In accordance with another embodiment of the present disclosure, a laboratory automation system is presented that can utilize the sample distribution system.

Accordingly, it is a feature of the embodiments of the present disclosure to provide a transport device, a sample distribution system and a laboratory automation system that are simple to handle. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
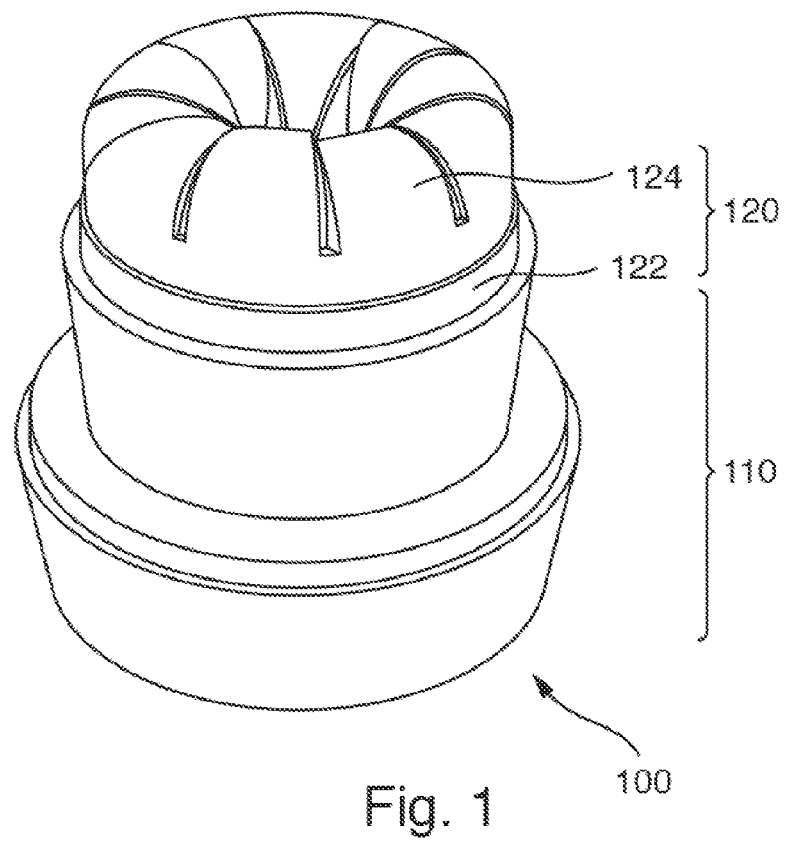
FIG. 1 illustrates a perspective view a transport device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A transport device for receiving and fixing a sample container from a predefined quantity of different sample containers is presented. The predefined quantity of different sample containers can be formed, for example, by a number of different types of sample tubes, wherein the different types differing, for example, in a diameter of the sample tube. The transport device is realized for receiving and fixing different sample containers, i.e. it is able to accommodate different types of sample containers or sample tubes.

The transport device can further serve for transporting the sample container between pre-analytical, analytical and/or post-analytical stations of a laboratory automation system. The transport device can be, for example, a sample carrier. A pre-analytical station usually serves for pre-processing samples or sample containers. An analytical station can be realized, for example, for the purpose of using a sample or part of the sample and a reagent in order to generate a measurable signal, on the basis of which it is possible to determine whether and, where applicable, in which concentration the analyte is present. A post-analytical station usually serves for post-processing samples or sample containers.

The pre-analytical, analytical and post-analytical stations can comprise, for example, at least one station from the list of following stations: a cap-removing station for removing caps or closures on sample tubes, a cap-positioning station for placing caps or closures in position on sample tubes, an aliquoting station for aliquoting samples, a centrifugal station for centrifuging samples, an archiving station for archiving samples, a pipetting station for pipetting, a sorting station for sorting samples or sample tubes, a sample tube type-determining station for determining a type of sample tube and a sample quality-determining station for determining a sample quality.

The transport device comprises at least one magnetically active element, for example in the form of one or several permanent magnets and/or in the form of ferromagnetic material. The magnetic element can interact with a magnetic field generated by at least one external actuator such that a magnetic driving force can be applied to the transport device or the magnetically active element.

The transport device can further comprise a holding unit with a push-through region, through which the sample container can be pushed in its longitudinal direction. The holding unit can be realized in such a manner that the sample tube, in the pushed-through state, can be fixed radially in the region of the holding unit.

The transport device can further comprise a receiving unit which can be spaced from the holding unit and can be realized for the purpose of receiving a bottom end of a pushed-through sample tube and fixing or stabilizing the bottom end in a radial manner.

A transport device can allow for, on the one hand, automated movement of the transport device, for example by a sample distribution system. On the other hand, the separation of the holding unit and the receiving unit can enable better tolerance against the sample container tipping up when the sample container is introduced into the transport device and withdrawn from the same such that improved automation of these operations can be achieved.

Sample containers or sample tubes can typically be realized in a radially symmetrical or axially symmetrical manner. This can mean that they can comprise a radial-symmetrical or axial-symmetrical cross section which usually can reduce along the longitudinal direction or longitudinal axis of the sample tube in the region of a longitudinal end of the sample container. The longitudinal direction can typically be substantially identical to or parallel with the axis of symmetry.

Typically, the receiving unit can receive a bottom end or longitudinal end, i.e. the bottommost part of the sample container. In other words, the receiving unit can carry the sample container. The holding unit, contrary to this, typically can hold a region of the sample container that can be higher up. The region can be secured against tipping to the side by the holding unit. The receiving unit can also form an end stop when the sample tube can be introduced or pushed through into the transport device through the holding unit.

The receiving unit can comprise an indentation or cavity in the form of a cone for receiving the bottom end of the sample tube such that sample tubes with different diameters can be held vertically in the transport device irrespective of the diameter. Consequently, the sample tube can be supported and laterally fixed.

The indentation can be realized tapering downward, i.e. away from the end, at least in portions. The indentation can be realized in a conical manner at least in portions or also completely. In this way, good adaptation to typical forms of sample containers can be achieved.

The indentation can correspond with the shape of the bottom end of a sample container. This can mean, for example, that the indentation can be realized in a complementary manner to the end of the sample container. Particularly secure reception can be achieved in this way.

The transport device can comprise a sliding portion with a circular cross section, along which the transport device can slide over a transport surface when the driving force is present. The permanent magnet can be arranged on an axis, or symmetrically with respect to an axis, which can extend through the center point of the circular cross section and which can stand substantially perpendicular on the cross section. The sliding portion can be realized in a flat manner. The cross section can be substantially perpendicular to a longitudinal direction of the sample container when the sample container is situated in the transport device.

The sliding portion can typically lie substantially parallel to the transport surface and can comprise a level under surface, as a result of which a movement of the transport device with reduced wear can be achievable over the transport surface. Arranging the permanent magnet in a central manner in the transport device can facilitate the actuation and movement of the transport device by externally applied magnetic fields.

According to one embodiment, the transport device can comprise a bottom part and a top part. The receiving unit can be realized on or in the bottom part and the holding unit can be realized on or in the top part. The bottom part and the top part can be releasable from one another. This can facilitate, for example, the production of the transport device, as the bottom part and the top part can be produced separately from one another and also correspondingly different methods and materials can be applied or used that are suitable in each case. In addition, it can be possible only to exchange one of the two parts insofar as only one of the two may be defective. This can reduce running costs. The bottom part and the top part can be connected together by a quick-release closure and can be correspondingly releasable from one another. In the case of an embodiment with a bottom part and a top part, the sliding portion can be a component part of the bottom part. Consequently, the sliding portion can rest on the transport surface.

According to an embodiment, the holding unit can comprise a number of, for example, ten, spring elements which can be realized for the purpose of acting upon the sample tube in each case with radially inwardly directed fixing forces. Such an embodiment can enable the sample tube to be introduced into the transport device in a guided manner, the spring elements being pressed lightly outward and stabilizing the sample tube even when the sample tube is not yet in contact with the receiving unit. In addition, the spring elements can allow for defined mobility of the sample tube, which, for example, in the event of the sample tube knocking against an obstacle, can prevent the sample tube from breaking. The spring elements can comprise a shape of downwardly open semicircles in cross section. Consequently they can be simply produced and bring about a centering of a sample tube to be introduced even before the spring forces act.

The spring elements can be fastened on a ring which can be held, for example, in an interference fit with the bottom part. The ring and the spring elements can together form the upper part. This can enable, for example, separate production of the spring elements including their ring using a suitable material and production method. The spring elements can tend toward wear and tear on account of the sample containers being frequently introduced and withdrawn. In such cases, the embodiment can allow for simple exchange of the spring elements including their ring without the rest of the transport device having to be exchanged.

According to an embodiment, the holding unit can be a collet. This embodiment can be an alternative to the embodiment with spring elements. The collet can make it possible to exert a defined radial pressure or to apply force in a radial manner onto the sample container and this can be adjustable.

The collet can comprise a number of clamping elements which can be arranged in a circular manner. A sleeve, which can be displaceable vertically between a top position and a bottom position, can be arranged radially outside of the clamping elements. The sleeve can press the clamping elements radially inward when situated in the top position. In one embodiment, six clamping elements arranged in a circular manner can be provided.

By the displaceable sleeve, the transport device can be influenced in a defined manner by an apparatus which can be suitable for this purpose and may not be associated with the transport device in order to determine whether the collet can exert a radial holding force onto the sample tube or not. For example, the sleeve can be pressed downward by an external device when the collet does not exert any radial force onto the sample tube. Such a state can be advantageous, for example, for the introducing and withdrawing of the sample tubes. Furthermore, the sleeve can be moved into the top position as a result of the external device or in another manner in order to achieve that the sample tube received in the transport device is held radially by the collet. Such a state can be advantageous, for example, for the displacing and mounting of a sample tube.

A spring, which can tension the sleeve toward the top position, can be arranged below the sleeve. Consequently, the sleeve can be in the top position when the transport device is not situated under the influence of an external device which can press the sleeve downward. Consequently, the sample tube can be fixed in a radial manner in the normal case. If a sample tube is to be introduced into the transport device or removed from the transport device, a device which can press the sleeve downward in order to release the sample tube can be sufficient. Once the operation has been terminated, the sleeve can be released again such that it can be pressed upward again by the spring and the collet can exert its stabilizing effect onto the sample tube again. This can enable simple loading and unloading of the transport device.

The holding unit and the receiving unit can be spaced apart from one another in such a manner that a maximum push-through depth can be about 2 cm. The push-through depth can also be designated as the insertion depth. This can be that depth by which a sample tube can still be moved downward when the sample tube has straight been pushed through the holding unit. A maximum push-through depth of 2 cm or approximately 2 cm can be advantageous in practice.

The transport device can comprise an overall height of approximately 4 cm. This has proved advantageous for many applications and can allow a compact design whilst at the same time providing a sufficient stabilizing effect for the sample tube. The maximum height of the transport device can correspond to its diameter. This can enable an embodiment which can be flat and sturdy against being tipped up.

The transport device can be realized in a rotationally symmetrical manner. This can enable simple production and can further avoid a direction such that the transport device can be moved along the transport surface in a two-dimensional manner using magnetic fields without consideration having to be given to a current orientation of the transport device.

Referring initially to FIG. 1, FIG. 1 shows a perspective view of a first exemplary embodiment of a transport device 100. The transport device 100 can comprise a bottom part 110 and a top part 120. The bottom part 110 and the top part 120 can be removable from one another. The top part 120, in turn, can be divided into a ring 122 and a total of ten spring elements 124.

Figure 2:
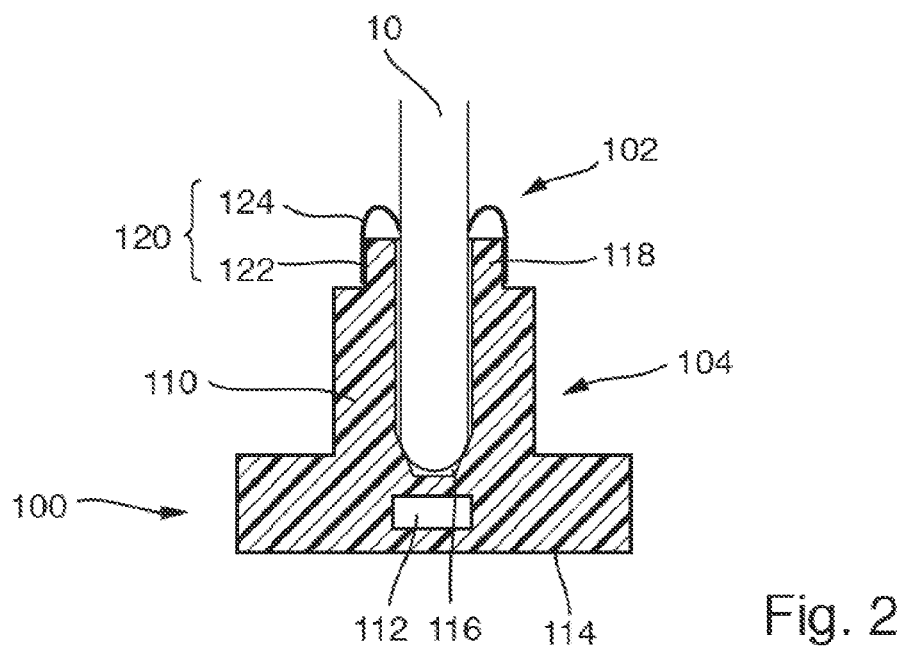
FIG. 2 illustrates a side sectioned view of the transport device of FIG. 1 according to an embodiment of the present disclosure.

The details of the transport device 100 are described in more detail below with reference to FIG. 2. FIG. 2 shows a side sectioned view of the transport device 100 of FIG. 1. Furthermore, a sample container in the form of a sample tube 10, which can be received in the transport device 100 for holding and transporting, can be situated in the transport device 100.

The bottom part 110 can comprise a permanent magnet 112 which can be arranged centrally in a sliding portion 114 with a level bottom surface. The sliding portion 114 can be realized for the purpose of resting on a transport surface. By the permanent magnet 112 and the sliding portion 114, the transport device 100 including the sample tube 10 can be moved over the transport surface of a sample distribution system when suitable magnetic fields are generated by the sample distribution system.

An indentation 116 in which the bottom end of the sample tube 10 is received can also be realized in the bottom part 110. The indentation 116 and the bottom end of the sample tube 10 can be realized in a complementary manner with respect to one another.

Furthermore, at its top end the bottom part 110 can comprise a projection 118, over which the ring 122 of the top part 120 can be pulled. The ring 122 can be held in an interference fit on the projection 118. This can make it possible for the ring 122 and consequently also the top part 120 to be reliably fastened on the bottom part 110. It can be provided at the same time that the top part 120 can be removed in a simple manner from the bottom part 110. Upwardly directed forces which overcome the holding forces generated by the interference fit have to be exerted onto the top part 120 for this purpose.

The spring elements 124 can be realized, for instance, as downwardly open semicircles. In this case, they can end at one end at the ring 122, whereas they can press at the other end against the sample tube 10. Consequently, they can exert an inwardly directed fixing force onto the sample tube 10. This can prevent the sample tube 10 from falling out or wobbling, but at the same time easily can allow the sample tube 10 to be introduced and removed and can also provide a certain tolerance should the sample tube 10 knock against an obstacle for example with its top surface.

The bottom part 110 with its conical indentation 116 can form a receiving unit 104 for the sample tube 10. The top part 120 with its spring elements 124 can form a holding unit 102 for the sample tube 10. Together the holding unit 102 and the receiving unit 104 can act in such a manner that the sample tube 10 can be held reliably in its position in the transport device 100 and in this way can be simple to transport.

Figure 3:
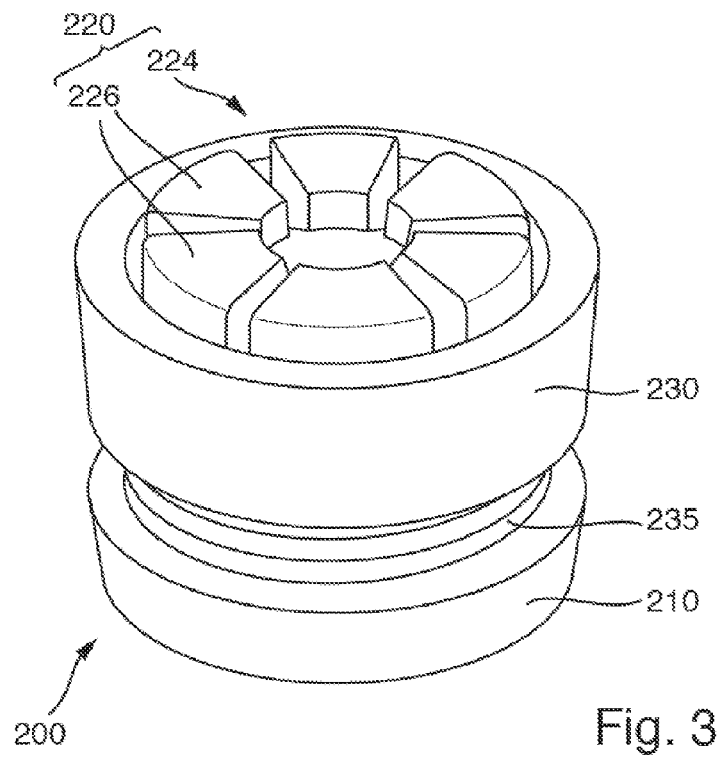
FIG. 3 illustrates a perspective view of a transport device according to another embodiment of the present disclosure.

FIG. 3 shows a perspective view of a second exemplary embodiment of a transport device 200. The transport device 200 can comprises a bottom part 210 and a top part 220. The top part 220 can comprise a collet 224 with a total of six clamping elements 226. A sleeve 230 with a spring 235 arranged below it can be situated radially outside of the top part 220.

Figures 4, 5:
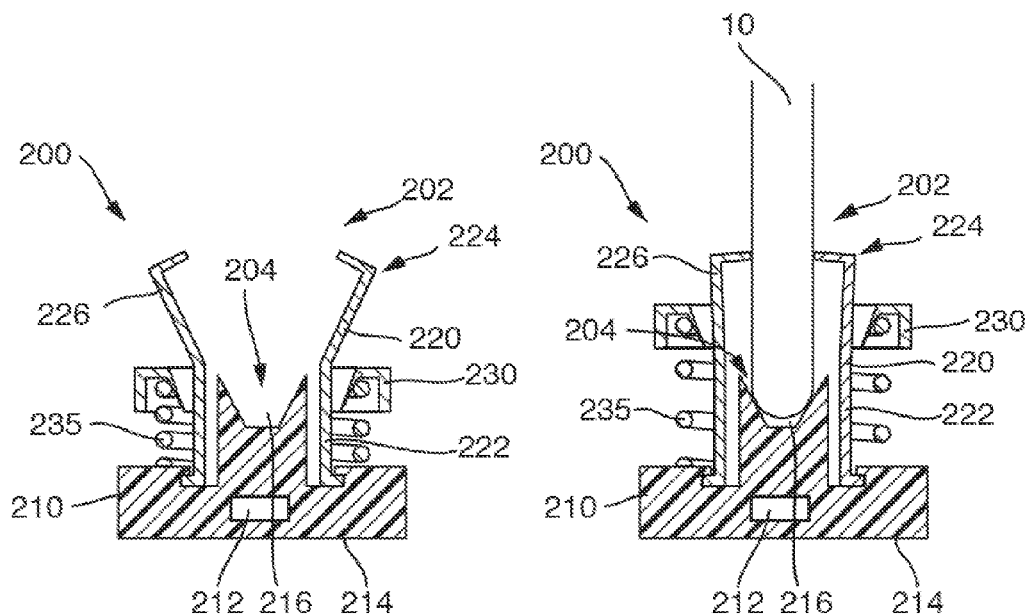
FIG. 4 illustrates a side sectioned view of the transport device of FIG. 3 in a first state according to an embodiment of the present disclosure.
FIG. 5 illustrates a side sectioned view of the transport device of FIG. 3 in a second state according to an embodiment of the present disclosure.

The details of the transport device 200 are described in more detail with reference to FIGS. 4 and 5. FIG. 4 shows a side sectioned view of the transport device 200 in a first state. The bottom part 210 can comprise a permanent magnet 212 and a sliding portion 214. The function thereof can be identical to that in the case of the transport device 100 according to the first exemplary embodiment and is consequently not described again at this point. The bottom part 210 can further comprise an indentation 216 which can be realized in a complementary manner to a bottom surface of a sample tube which is to be received.

The top part 220 can comprise a ring 222 which can be hooked in the bottom part 210. This can mean that the ring 222 can remain in its shown position with reference to the bottom part 210 until it can be pressed radially inward on its bottom side. In this case, a positive locking connection can be released and the top part 220 can be removed upward from the bottom part 210. This can also be designated as a locking connection.

The upper part 220 can comprise the collet 224 above the ring 222. The collet 224 can comprise a total of six clamping elements 226 as shown in FIG. 3. In FIG. 4, the clamping elements 226 can project radially outward such that a distance between respective oppositely situated clamping elements can be greater than a maximum diameter of the indentation 216. This state can be used for the purpose of introducing a sample tube 10 into the transport device 200 or removing it from the transport device.

The sleeve 230 can be situated in the state shown in FIG. 4 substantially below the collet 224. This can correspond to a bottom position. A spring 235 which can be a helical spring can be situated between the bottom part 210 and the sleeve 230. It can press the sleeve 230 upward away from the bottom part 210. This can mean that the state shown in FIG. 4 can only be assumed as a result of the sleeve 230 being pressed downward against the force of the spring 235 by a device or manually. Such a force can be exerted, for example, by a device which can be provided for generating the state shown in FIG. 4. Loading and unloading can be possible in the state.

The bottom part 210 and its indentation 216 can form a receiving unit 204. The top part 220 and its collet 224 can form a holding unit 202. Together the holding unit 202 and the receiving unit 204 can act as a holder for a sample tube 10, as is shown in FIG. 5.

In the state shown in FIG. 5, the sleeve 230 can be situated in its top position. Consequently, the sleeve 230 can press the clamping elements 226 radially inward onto the sample tube 10 which can then be fixedly received in the transport device 200. The spring 235 can ensure that the sleeve 230 can be situated in its top position insofar as no downwardly directed force acts on the sleeve 230. This is the case, for example during normal transport operations or storage periods.

The sample tube 10 can then lie in the trough or the cone 216 and as a result can be supported both downward and can also be stabilized in a radial manner. The collet 224 with its clamping elements 226 can also have a radially fixing effect further up such that the sample tube 10 cannot tip up.

The exemplary embodiments of transport devices shown can be used with a sample distribution system. The transport devices, in this connection, can form the sample carriers. The transport devices, the sample distribution system and a number of pre-analytical, analytical and/or post-analytical stations can form a laboratory automation system.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A transport device for receiving and fixing a sample container and for transporting the sample container between pre-analytical, analytical and/or post-analytical stations of a laboratory automation system, the transport device comprises:
    at least one magnetically active element, wherein the at least one magnetically active element interacts with a magnetic field such that a driving force is applied to the transport device, and wherein the magnetic field is generated by at least one electromagnetic actuator;
    a holding unit having a push-through region through which the sample container can be pushed in longitudinal direction, wherein the holding unit is formed such that the sample container, in the pushed-through state, is fixed radially in the region of the holding unit, and wherein the holding unit is a collet, wherein the collet comprises a plurality of clamping elements arranged in a circular manner, wherein a sleeve, displaceable vertically between a top position and a bottom position, is arranged radially outside of the clamping elements, wherein the sleeve presses the clamping elements radially inward when situated in the top position, and wherein a spring, which tensions the sleeve toward the top position, is arranged below the sleeve; and
    a receiving unit spaced from the holding unit, the receiving unit comprising a conical indentation for receiving a bottom end of the sample container, wherein the receiving unit receives the bottom end of a pushed-through sample container and wherein the receiving unit is fixed to the bottom end of a pushed-through sample container in a radial manner.

2. The transport device according to claim 1, further comprising,
    a sliding portion having a circular cross section along which the transport device slides over a transport surface when the magnetic driving force is present.

3. The transport device according to claim 1, further comprising,
    a bottom part; and
    a top part, wherein the receiving unit is formed on the bottom part and the holding unit is formed on the top part and wherein the bottom part and the top part are releasable from one another by a quick-release closure.

4. The transport device according to claim 1, wherein the holding unit and the receiving unit are spaced apart from one another so that a maximum insertion depth of the sample container into the conical indentation of the receiving unit is two centimeters.

* * * * *